United States Patent [19]

Adams et al.

[11] Patent Number: 5,332,823
[45] Date of Patent: Jul. 26, 1994

[54] CERTAIN THREE COMPONENT IONIC SUBSTITUTED PYRIDINE COMPOUNDS AS INTERMEDIATES

[75] Inventors: Charles D. Adams, Newark; Greg A. Bullock, Hockessin; George C. Chiang, Wilmington, all of Del.

[73] Assignee: E. I. Du Pont de Nemours and Company, Wilmington, Del.

[21] Appl. No.: 61,394

[22] Filed: May 13, 1993

Related U.S. Application Data

[62] Division of Ser. No. 728,446, Jul. 11, 1991, Pat. No. 5,235,060.

[51] Int. Cl.$^5$ .................. C07D 213/70; C07D 213/56
[52] U.S. Cl. .................................. 546/291; 546/294; 546/298; 546/296; 546/316

[58] Field of Search ............... 546/294, 298, 296, 315, 546/318, 291, 316

[56] References Cited

FOREIGN PATENT DOCUMENTS

WO89/01937  9/1989  PCT Int'l Appl. ................ 544/331

OTHER PUBLICATIONS

R. W. Lang et al., *Helvetica Chimica Acta*, 71:596–601 (1988).

*Primary Examiner*—Alan L. Rotman

[57] ABSTRACT

The present invention relates to novel substituted pyridine compounds useful as intermediates in the preparation of herbicidal compounds and the process for the preparation of said pyridine compounds.

11 Claims, No Drawings

CERTAIN THREE COMPONENT IONIC SUBSTITUTED PYRIDINE COMPOUNDS AS INTERMEDIATES

This is a division of application Ser. No. 07/728,446, filed Jul. 11, 1991, now U.S. Pat. No. 5,235,060.

FIELD OF THE INVENTION

The present invention relates to novel substituted pyridine compounds and a process for their preparation.

BACKGROUND OF THE INVENTION

The sulfonylurea herbicides are an extremely potent class of herbicides discovered relatively recently which generally consist of a sulfonylurea bridge, —$SO_2NH$-CONH—, linking two aromatic or heteroaromatic rings. Such herbicides have become commercially important. There is, therefore, a continuing need to discover new processes for their preparation that offer advantages that add to their commercial desirability.

WO 89/01937 genetically discloses, in part, certain compounds of Formula I as intermediates to pyridine sulfonylureas.

Lang, R. W. and Wenk, P. F., *Helvetica Chimica Acta*, 1988, 71, 596–601 also teaches the preparation of ethyl 1,2-dihydro-2-oxo-6-(trifluoromethyl)-3-pyridinecarboxylate

SUMMARY OF THE INVENTION

This invention pertains to substituted pyridines of Formula I and a process for their preparation. Compounds of Formula I are prepared by the reaction of enones of Formula II with acetonitrile derivatives of Formula III, under basic conditions, to yield enol salts of Formula IV, which following treatment with acid give compounds of Formula I as shown in Equations 1 and 2.

$$R^1OC(=O)C(R^2)=CHCR^3 + NCCH_2-R^4 \xrightarrow{\text{base}} \left[ \begin{array}{c} CN\ R^2\quad R^3 \\ |\quad |\quad\ \ | \\ C=C-CH=CO \\ | \\ R^4 \end{array} \right]_n M \quad 1)$$

II    III    IV $$\left[ \begin{array}{c} CN\ R^2\quad R^3 \\ |\quad |\quad\ \ | \\ C=C-CH=CO \\ | \\ R^4 \end{array} \right]_n M \xrightarrow{\text{acid}} \text{(pyridine I)} \quad 2)$$

IV    I wherein:

$R^1$ is selected from the group $C_1$-$C_4$ alkyl;

$R^2$ is selected from the group hydrogen, $C_1$-$C_3$ alkyl optionally substituted with methoxy or 1-3 fluorine and $C_1$-$C_2$ alkoxy optionally substituted with 1-3 fluorine;

$R^3$ is selected from the group $C_1$-$C_3$ alkyl substituted with methoxy or 1-3 fluorine;

$R^4$ is selected from the group $SO_2R^5$, $CO_2R^5$ and $C(O)N(R^6)_2$;

$R^5$ is selected from the group $C_1$-$C_2$ alkyl optionally substituted with $C_1$-$C_2$ alkoxy or 1-3 halogens independently selected from the group chlorine and fluorine;

$R^6$ is independently selected from the group hydrogen and $C_1$-$C_2$ alkyl;

M is selected from the group Li, Na, K, Mg, Ca and $NH_4$ or alkyl substituted ammonium;

X is selected from the group Br and OH; and n is 1 or 2.

provided that when the process of Equation 2 is carried out under anhydrous conditions the acid used is HBr (X is Br).

The compounds of the invention are the Compounds of Formula I and IV (Formula I: pyridine ring with $R^2$, $R^3$, $R^4$, X, N substituents)

$$\left[ \begin{array}{c} CN\ R^2\quad R^3 \\ |\quad |\quad\ \ | \\ C=C-CH=CO \\ | \\ R^4 \end{array} \right]_n M \quad IV$$

wherein:

$R^2$, $R^3$, $R^4$, M and n are as previously defined; provided that when X is Br or OH, and $R^3$ is $CF_3$ and $R^4$ is $CO_2CH_3$, then $R^2$ is other than hydrogen.

In the above definitions, the term "alkyl" or "alkoxy" denotes a straight or branched carbon chain, e.g., methyl, ethyl, n-propyl, isopropyl or the different butyl isomers. The number of carbon atom allowed in the substituent group, not including optional substituents, is indicated by the "$C_i$-$C_j$" prefix where i and j are numbers from 1 to 4.

The terms "acid" or "protic acid" are used interchangeably and are defined as proton-donating acids such as HBr, HCl, $H_2SO_4$, $HNO_3$, $H_3PO_4$ and the like.

The reaction conditions for Equations 1 and 2 are generally as follows:

| Equation 1 | |
|---|---|
| Solvents: | Toluene, xylenes, acetonitrile, water, lower alcohols such as methanol and ethanol, and esters of organic acid such as methyl, ethyl and propyl acetate. |
| Preferred Solvents: | Toluene and xylenes. |
| Bases: | KOH, NaOH, NaOMe, $Na_2CO_3$, $K_2CO_3$, $NH_3$, triethylamine, $Ca(OH)_2$, and $Mg(OH)_2$. |
| Preferred Bases: | KOH, $K_2CO_3$, and NaOH. |
| Equivalents of Base: | 1-2 moles based on moles of III. |
| Preferred Equivalents: | 1-1.1. |
| Temperatures: | 10–100° C. |
| Preferred Temperatures: | 20–60° C. |
| Time: | 0.1–18 hours. |
| Preferred Time: | 2-5 hours. |
| Pressure: | 0.25-5 atm. |
| Preferred pressure: | 1 atm. |
| Equation 2 | |
| Solvents: | Lower organic acids such as acetic and propionic acids, water, dioxane, diethyl ether, lower alcohols, methyl acetate, ethyl acetate and methylene chloride. |
| Preferred Solvents: | Acetic acid, propionic acid, water and methyl acetate. |
| Acids: | HBr or other protic acids. |
| Preferred Acids: | HBr and HCl. |
| Equivalents of Acid: | 1-10 moles based on moles of IV. |

| | |
|---|---|
| Preferred equivalents: | 3-5. |
| Temperatures: | −10-90° C. |
| Preferred Temperatures: | −10-40° C. |
| Time: | 0.1-24 hours. |
| Preferred Time: | 0.5-3 hours. |
| Pressure: | 0.25-5 atm. |
| Preferred pressure: | 1 atm. |

Accordingly the process of the invention is a process for preparing compounds of Formula IV comprising reacting enones of Formula II with acetonitrile derivatives of Formula III under basic conditions in the presence of a solvent at a temperature of 10°-100° C. for 0.1-18 hours and a pressure of 1-5 atmospheres as indicated in the Equations that follows:

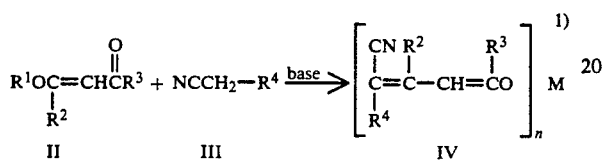

wherein:
$R^1$ is selected from the group $C_1-C_4$ alkyl;
$R^2$ is selected from the group hydrogen, $C_1-C_3$ alkyl optionally substituted with methoxy or 1-3 fluorine and $C_1-C_2$ alkoxy optionally substituted with 1-3 fluorine;
$R^3$ is selected from the group $C_1-C_3$ alkyl substituted with methoxy or 1-3 fluorine;
$R^4$ is selected from the group $SO_2R^5$, $CO_2R^5$ and $C(O)N(R^6)_2$;
$R^5$ is selected from the group $C_1-C_2$ alkyl optionally substituted with $C_1-C_2$ alkoxy or 1-3 halogens independently selected from the group chlorine and fluorine;
$R^6$ is independently selected from the group hydrogen and $C_1-C_2$ alkyl;
M is selected from the group Li, Na, K, Mg, Ca, $NH_4$ or alkyl substituted ammonium; and
n is 1 or 2
and then treating the compound of Formula IV with a protic acid in the presence of a solvent at a temperature of −10°-90° C. for 0.1-24 hours at 0.25 to 5 atmospheres to form a compound of Formula I as indicated in the following equation:

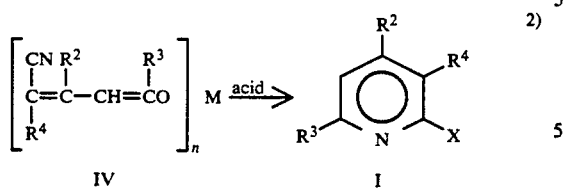

wherein:
$R^1$ is selected from the group $C_1-C_4$ alkyl;
$R^2$ is selected from the group hydrogen, $C_1-C_3$ alkyl optionally substituted with methoxy or 1-3 fluorine and $C_1-C_2$ alkoxy optionally substituted with 1-3 fluorine;
$R^3$ is selected from the group $C_1-C_3$ alkyl substituted with methoxy or 1-3 fluorine;
$R^4$ is selected from the group $SO_2R^5$, $CO_2R^5$ and $C(O)N(R^6)_2$;
$R^5$ is selected from the group $C_1-C_2$ alkyl optionally substituted with $C_1-C_2$ alkoxy or 1-3 halogens independently selected from the group chlorine and fluorine;
$R^6$ is independently selected from the group hydrogen and $C_1-C_2$ alkyl;
M is selected from the group Li, Na, K, Mg, Ca, $NH_4$, and alkyl substituted $NH_4$;
X is selected from the group Br and OH; and
n is 1 or 2
provided that when the process of Equation 2 is carried out under conditions so that when less than 3 moles of water are present the acid used is HBr.

Preferred processes are:
1) The process of Equation 1.
2) The process of Equation 2.
3) The process of Preferred 1 wherein $R^2$ is hydrogen, $R^3$ is $CF_3$, $R^4$ is $CO_2CH_3$, the solvent is toluene and the base is KOH (M is K).
4) The process of Preferred 2 wherein $R^2$ is hydrogen, $R^3$ is $CF_3$, $R^4$ is $CO_2CH_3$, the solvent is methyl acetate and the acid is HBr (X is Br).
5) The process of Preferred 2 wherein $R^2$ is hydrogen, $R^3$ is $CF_3$, $R^4$ is $CO_2CH_3$, the solvent is water and the acid is HBr or HCl (X is OH).

The preferred compounds of Formula I are compounds wherein:
6) $R^3$ is $CF_3$, $R^4$ is $SO_2R^5$ and $R^5$ is ethyl.
7) $R^3$ is $CF_3$, $R^4$ is $C(O)N(R^6)_2$ and $R^6$ is $CH_3$.
8) The compounds of Preferred 6 wherein $R^2$ is H.
9) The compounds of Preferred 7 wherein $R^2$ is H.

The preferred compounds of Formula IV are compounds wherein:
10) M is K or Na, $R^3$ is $CF_3$, $R^4$ is $CO_2R^5$, $R^5$ is $CH_3$, and n is 1.
11) M is K or Na, $R^3$ is $CF_3$, $R^4$ is $SO_2R^5$, $R^5$ is ethyl, and n is 1.
12) M is K or Na, $R^3$ is $CF_3$, $R^4$ is $C(O)N(R^6)_2$, $R^6$ is $CH_3$, and n is 1.
13) The compounds of Preferred 10 wherein $R^2$ is H.
14) The compounds of Preferred 11 wherein $R^2$ is H.
15) The compounds of Preferred 12 wherein $R^2$ is H.

DETAILED DESCRIPTION OF THE INVENTION

The present invention pertains to novel substituted pyridines and a process for their preparation. The compounds of the invention are useful as intermediates in the preparation of commercial herbicides. The process of the present invention permits more efficient herbicide production.

It has been found that unsaturated ketones of Formula II react with acetonitrile derivatives of Formula III in the presence of a base to give novel enolate salt compounds (IV). This is shown in Equation (A):

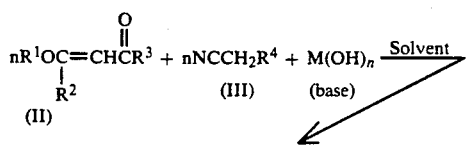

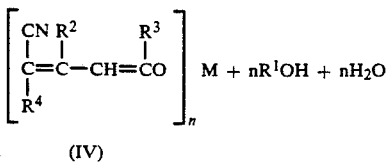

(IV)

wherein:
$R^1$ is selected from the group $C_1-C_4$ alkyl;
$R^2$ is selected from the group hydrogen, $C_1-C_3$ alkyl optionally substituted with methoxy or 1-3 fluorine and $C_1-C_2$ alkoxy optionally substituted with 1-3 fluorine;
$R^3$ is selected from the group $C_1-C_3$ alkyl substituted with methoxy or 1-3 fluorine;
$R^4$ is selected from the group $SO_2R^5$, $CO_2R^5$ and $C(O)N(R^6)_2$;
$R^5$ is selected from the group $C_1-C_2$ alkyl optionally substituted with $C_1-C_2$ alkoxy or 1-3 halogens independently selected from the group chlorine and fluorine;
$R^6$ is independently selected from the group hydrogen and $C_1-C_2$ alkyl;
M is selected from the group Li, Na, K, Mg, Ca, and $NH_4$ or alkyl substituted ammonium;
when M is Mg or Ca, n is 2 and 1 otherwise.

Bases which include alkali metal hydroxides, alkali metal carbonates, alkaline earth hydroxides, ammonia, and alkyl amines can be used. Preferred bases are KOH, NaOH and $K_2CO_3$. Equivalents of base can vary between 1.0 and 2.0 per mole of (III). The preferred equivalent range is 1.0 to 1.1.

A wide variety of solvents can be used for Equation A. These include water, lower alcohols, esters, ketones, methyl cyanoacetate, toluene, and xylene. It is also possible to operate without any solvent when either (II) or (III), or both, are liquids. Although the reaction proceeds in a variety of solvents, as evidenced by the appearance of the characteristic yellow color of (IV), toluene, water, isopropanol, and n-butanol are preferred solvents. Compound (IV) precipitates in these solvents and can be recovered easily by filtration.

Temperatures can be from 10° C. up to 100° C., depending on the boiling point of the solvent; the preferred temperature range is 20° C. to 60° C. The reaction is exothermic, and cooling will be needed to maintain the temperature range when operating on a large scale. Reaction times can be as short as 5 minutes or as long as 18 hours. The preferred time range is 2 to 5 hours. The reaction has been run at atmospheric pressure, and this is preferred. However, it could be run at higher pressures up to 5 atmospheres or lower pressures down to 200 mm Hg if this were required.

It has been found also that when enolate salts of structure (IV) are exposed to strong acids, they cyclize to form novel substituted pyridine compounds (I), as shown by Equation (B):

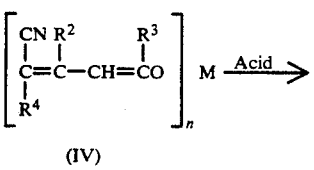

(B)

(IV)

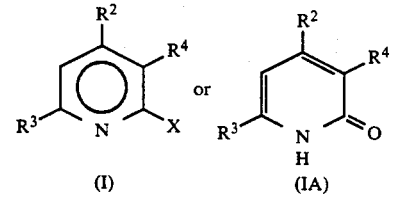

(I)  (IA)

where $R^2$, $R^3$, $R^4$ and M and n are as before, and X is bromine or hydroxy. When X is hydroxy, the possibility exists that the tautomeric isomer, IA, will also be present. When the acid is HBr and less than 3 moles of water are present, X is bromo. Since the enol salts typically contain 3 to 10 weight percent water when recovered, vacuum drying can be beneficial. Br is also favored if a water scavenger such as trifluoroacetic anhydride is present in the reaction mass. If water is present beyond any amount that may be formed by the cyclization itself, there will be an increasing tendency for X to be hydroxy.

Solvents that can be used include acetic acid, methylene chloride, water, dioxane, diethyl ether, esters of lower alcohols, and toluene. If it is desired that X be bromo, the water content should be as low as possible. If it is desired that X be hydroxy, at least one equivalent of water based on (IV) must be present. Preferred solvents are acetic acid, water, and methyl acetate.

While HBr and HCl are preferred, other strong protic acids may be used. The amount of acid should be 1 to 10 equivalents based on (IV); the preferred range is 3 to 5 equivalents. Temperatures may be in the −10° C. to 90° C. range with the preferred range from −10° C. to 40° C. The time can be from 5 minutes to 24 hours. The preferred time range is 30 minutes to 3 hours. Pressures have been 1 atmosphere. However, they could be higher up to 5 atmospheres or lower down to 200 mm Hg if this were desired.

The following examples illustrate the invention. The required ketone starting materials (II) can be prepared as described in *Helv. Chimica Acta*, 71, 596–601 (1988) or *Synthesis*, 1016–17 (1986). Several of the starting materials (III) are commercially available or easily prepared by known procedures or slight modifications thereof.

EXAMPLE 1

Peparation of Enolate Salt (IV) Where $R^4$ is Methyl Carboxy, $R^2$ is Hydrogen, and $R^3$ is Trifluoromethyl Methyl cyanoacetate (1 mL, 11.3 mmoles), 4-butoxy-1,1,1-trifluoro-3-buten-2-one (2 mL, 11.4 mmoles) and 1.6 g (11.6 mmoles) $K_2CO_3$ were added to 5 mL water. The mixture was kept for an hour with occasional shaking. The yellow precipitate was collected by filtration, washed with water and n-butyl chloride, and dried at room temperature. This gave 1.5 g of enol salt that contained 4.1% water by Karl Fischer titration. This is a 49% yield when corrected for water content.

EXAMPLE 2

Preparation of Enolate Salt (IV) Where $R^4$ is Methyl Carboxy, $R^2$ is Hydrogen, and $R^3$ is Trifluoromethyl Methyl cyanoacetate (11.2 g, 0.113 moles), 4-butoxy-1,1,1-trifluoro-3-buten-2-one (22.5 g of 93%, 0.107 moles), and 8.2 g (0.124 moles) of 85% KOH in 10 mL of water were added to 90 mL of n-butanol. A yellow precipitate formed within a few minutes. The slurry was left to stand overnight before filtration. The solids were washed with 10 mL n-butanol and dried at room temperature. This gave 12.2 g of enolate salt, which is a 44% yield uncorrected for any water content.

EXAMPLE 3

Preparation of Enolate Salt (IV) Where $R^4$ is Methyl Carboxy, $R^2$ is Hydrogen, and $R^3$ is Trifluoromethyl Butyl vinyl ether (24.5 g, 0.244 moles) and pyridine (7.6 g, 0.096 moles) were added to 120 mL of toluene. The solution was held at 10° C. while 61.3 g (0.292 moles)of trifluoroacetic anhydride was added. The anhydride was rinsed in with 50 mL toluene. The resulting solution was stirred for 30 minutes. It was then washed twice with water and once with 5% NaHCO$_3$ solution. The toluene layer weighed 181 g and contained by gas chromatography analysis 18.1% of 4-butoxy-1,1,1-trifluoro-3-buten-2-one, which is a 69% field based on butyl vinyl ether.

To 150 g (0.139 moles) of this ketone solution were added 13.7 g (0.138 moles) of methyl cyanoacetate, 75 mL toluene, and 8.87 g (0.135 moles) of 85% KOH. The resulting yellow slurry exothermed from 28° C. to 45° C. during about 30 minutes. The temperature was maintained at 43° C. for 1.5 hours, and the slurry was stirred at ambient temperature for 3 hours. Filtration and drying on the filter gave 33.2 g of enolate salt which contained 3.2% water. This is a yield of 92% based on KOH when corrected for water content.

The NMR spectrum in (CD$_3$)$_2$SO gave a methyl singlet at 3.6 ppm and vinyl doublets at 5.6 and 8.2 ppm. There was also a water singlet at 3.3 ppm.

EXAMPLE 4

Preparation of (I) Where $R^2$ is Hydrogen, $R^3$ is Trifluoromethyl, X is Hydroxy, and $R^4$ is Methyl Carboxy The dried enolate salt prepared by the method of Example 3 (5.00 g, 0.019 moles) was added at 25° C. to 20 mL of 36% HCl. The resulting mixture was stirred for an hour at approximately 25° C., then 30 mL of water was added. The resulting mixture was stirred 45 minutes and filtered. The solids were dried on the filter to give 1.15 g of methyl 2-hydroxy-6-(trifluoromethyl)-3-pyridinecarboxylate (27% yield). The NMR spectrum in (CD$_3$)$_2$SO showed a singlet at 3.9 ppm (methyl), doublets at 7.5 and 8.3 ppm (pyridine ring hydrogens), and a broad singlet at 12.6 ppm (OH or NH).

EXAMPLE 5

Preparation of (I) Where $R^2$ is Hydrogen, $R^3$ is Trifluoromethyl, X is Bromine, and $R^4$ is Methyl Carboxy A portion (26.9 g, 0.104 moles) of enolate salt from Example 3 was added over about 5 minutes to a solution of 43 g (0.531 moles) HBr in 100 mL of acetic acid. The temperature exothermed from 22° C. to 26° C. as a result. The resulting slurry was stirred for an hour at approximately 23° C., then 100 mL of methylene chloride and 500 mL of cold water were added. The methylene chloride layer was washed with water (2×100 mL) and 5% sodium bicarbonate solution (1×100 mL). The methylene chloride solution was dried over a few grams of magnesium sulfate and then concentrated under reduced pressure, first using the aspirator and then the maximum vacuum obtainable with a mechanical pump.

This gave 14.6 g of an amber oil that contained no detectable methylene chloride by gas chromatographic analysis. A toluene solution of the oil (100 mg in 5 mL) gave a gas chromatograph that showed, excluding the toluene peak, 97.4 area percent attributed to methyl 2-bromo-6-(trifiuoromethyl)-3-pyridinecarboxylate, 2.6 area percent attributed to methyl 2-hydroxy-6-(trifiuoromethyl)-3-pyridinecarboxylate and no other significant peaks. The column was a capillary 10-meter HP-5 (5% phenyl-methyl silicone). The temperature was programmed as follows: 45° C. for 2 minutes, to 130° C. at 20° C. per minute, and held at 130° C. for 15 minutes. The injection port temperature was 225° C. The 2-hydroxy retention time was 6.47 minutes and the 2-bromo retention time was 6.83 minutes.

The NMR spectrum in (CD$_3$)$_2$SO showed a methyl singlet at 4.0 ppm and pyridine ring doublets at 8.2 and 8.5 ppm. Very small peaks for the 2-hydroxy compound could also be seen at 3.9, 7.5, and 8.3 ppm.

EXAMPLE 6

Preparation of (I) Where $R^2$ is Hydrogen, $R^3$ is Trifluoromethyl, X is Bromine, and $R^4$ is Methyl Carboxy Enol salt (20.0 g containing 3.8% water, 0.074 moles) made by the method of Example 3 was added at 25° C. to 130 g of 23% HBr in propionic acid. The resulting slurry was stirred for an hour at 25° C. It was then heated to 85° C. over 45 minutes. Heating and stirring were stopped, and the slurry was then left to stand for 16 hours at ambient temperature.

Methylene chloride (100 mL) was added, and the mixture was cooled briefly in an external ice bath. Ice water (300 mL) was added and the mixture was transferred to a separatory funnel where the lower layer was decanted. The water layer was extracted with another 20 mL of methylene chloride. The combined methylene chloride extracts were washed with ice water (2×100 mL) and cold 5% NaHCO$_3$ solution (1×100 mL), dried over a few grams of MgSO$_4$, and concentrated at 50° C., first with an aspirator and then with the maximum vacuum obtainable with a mechanical pump.

This gave 14.2 g of a red oil. Analysis by gas chromatography showed that the oil contained 13.2 area percent attributed to propionic acid, 1.6 area percent attributed to methyl 2-hydroxy-6-(trifiuoromethyl)-3-pyridinecarboxylate, 83.7 area percent attributed to methyl 2-bromo-6-(trifiuoromethyl)-3-pyridinecarboxylate, and several very small peaks. The column was the same as in Example 5. The temperature program was 95° C. for 5 minutes, to 130° C. at 15° C. per minute, for 6.81 minutes. The amount of propionic acid was quantified using 1,2-dichlorobenzene as internal standard and was found to be 9.9 weight percent. The NMR spectrum of the oil in (CD$_3$)$_2$SO showed a methyl singlet at 4.0 ppm and pyridine ring doublets at 8.1 and 8.5 ppm. There were also peaks for propionic acid at 1.0 and 2.3 ppm. Peaks for 2-hydroxy compound were very small.

EXAMPLE 7

Preparation of (I) Where $R^2$ is Hydrogen, $R^3$ is Trifluoromethyl, X is Bromine, and $R^4$ is Methyl Carboxy Enol salt made by the method of Example 3 (25.9 g containing 3.8% water, 0.096 moles) was added at 5° C.

to 173 g of 25.2% HBr in methyl acetate. An exotherm to 25° C. occurred. The resulting slurry was stirred for an hour. It was then added to 427 g of ice cold 3.2% NaOH and 100 ml of methylene chloride. The organic phase was decanted. The water phase was extracted with another 100 ml methylene chloride. The combined organic phase were washed with ice water (2×100 mL), dried over a little anhydrous MgSO$_4$ and concentrated at 50° C., first with an aspirator and then with the maximum vacuum obtainable with a mechanical pump.

This gave 19.8 g of a dark red oil. Analysis by gas chromatography showed 97.8 area percent for methyl 2-bromo-6-(trifluoromethyl)-3-pyridinecarboxylate, excluding the solvent (toluene) peak.

Reversed-phase liquid chromatographic (RPLC) analysis was performed utilizing a 25 cm Whatman Partisil C-8 column. A gradient mobile phase was used, with a ramp from 5% CH$_3$CN/pH 3.0 H$_2$O (H$_3$PO$_4$) to 100% CH$_3$CN/pH 3.0 H$_2$O (H$_3$PO$_4$) over 30 minutes (flow—2 mL/min; column temperature—40° C.; detector wavelength—220 nm). The sample solution contained 6.65 mg/mL of sample in neat CH$_3$CN. The peak attributed to 2-bromo was 93.5 area percent.

Compound I can be used to prepare sulfonylurea herbicides such as methyl 2-[[[[(4,6-dimethoxy-2-pyrimidinyl)-amino]carbonyl]amino]sulfonyl]-6-(trifluoromethyl)-3-pyridinecarboxylate and certain compounds of WO 89/01937 and U.S. Ser. No. 07/666,109.

What is claimed is:

1. A compound according to Formula I and IV

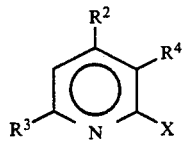

I

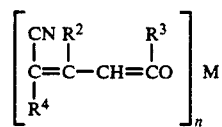

IV wherein:
R$^2$ is selected from the group hydrogen, C$_1$-C$_3$ alkyl optionally substituted with methoxy or 1-3 fluorine and C$_1$-C$_2$ alkoxy optionally substituted with 1-3 fluorine;
R$^3$ is selected from the group C$_1$-C$_3$ alkyl substituted with methoxy or 1-3 fluorine;
R$^4$ is selected from the group SO$_2$R$^5$ and C(O)N(R$^6$)$_2$;
R$^5$ is selected from the group C$_1$-C$_2$ alkyl optionally substituted with C$_1$-C$_2$ alkoxy or 1-3 halogens independently selected from the group chlorine and fluorine;
R$^6$ is C$_1$-C$_2$ alkyl;
M is selected from the group Li, Na, K, Mg, Ca, NH$_4$ and alkyl substituted NH$_4$;
X is selected from the group Br and OH; and
n is 1 or 2.

2. A compound of claim 1 Formula I wherein R$^3$ is CF$_3$, R$^4$ is SO$_2$R$^5$ and R$^5$ is ethyl.

3. A compound of claim 1 Formula I wherein R$^3$ is CF$_3$, R$^4$ is C(O)N(R$^6$)$_2$ and R$^6$ is CH$_3$.

4. A compound of claim 2 Formula I wherein R$^2$ is H.

5. A compound of claim 3 wherein R$^2$ is H.

6. A compound of claim 1 Formula IV wherein M is K or Na, R$^3$ is CF$_3$, R$^4$ is SO$_2$R$^5$ and C(O)N(R$^6$)$_2$, R$^5$ is CH$_3$, and n is 1.

7. A compound of claim 1 Formula IV wherein M is K or Na, R$^3$ is CF$_3$, R$^4$ is SO$_2$R$^5$, R$^5$ is ethyl, and n is 1.

8. A compound of claim 1 Formula IV wherein M is K or Na, R$^3$ is CF$_3$, R$^4$ is C(O)N(R$^6$)$_2$, R$^6$ is CH$_3$, and n is 1.

9. A compound of claim 6 wherein R$^2$ is H.

10. A compound of claim 7 wherein R$^2$ is H.

11. A compound of claim 8 wherein R$^2$ is H.

* * * * *